United States Patent [19]

Wideman et al.

[11] 4,367,358

[45] Jan. 4, 1983

[54] METHOD FOR THE PRODUCTION OF ETHYLBENZENE

[75] Inventors: Lawson G. Wideman, Tallmadge; Lynn A. Bente, Dover; Joseph A. Kuczkowski, Munroe Falls, all of Ohio

[73] Assignee: The Goodyear Tire & Rubber Company, Akron, Ohio

[21] Appl. No.: 330,059

[22] Filed: Dec. 14, 1981

[51] Int. Cl.³ .................................................. C07C 4/02
[52] U.S. Cl. ..................................... 585/440; 585/430
[58] Field of Search ................................. 585/430, 440

[56] References Cited

U.S. PATENT DOCUMENTS

| | | | |
|---|---|---|---|
| 3,461,183 | 8/1969 | Hepp et al. | 585/430 |
| 3,894,110 | 7/1975 | Drehmen et al. | 585/430 |
| 4,243,826 | 1/1981 | Antos | 585/440 |
| 4,322,556 | 3/1982 | Patterson et al. | 585/440 |

*Primary Examiner*—Curtis R. Davis
*Attorney, Agent, or Firm*—Bruce Hendricks

[57] ABSTRACT

A method for the production of ethylbenzene by catalytic dehydrogenation of cycloolefins having 8 carbon atoms and two double bonds which is present in a styrene stream. The method is carried out at a temperature from about 160° C. to about 450° C. by passing the stream over an alkali metal complex catalyst.

15 Claims, No Drawings

METHOD FOR THE PRODUCTION OF ETHYLBENZENE

BACKGROUND OF THE INVENTION

The field of this invention is related to the production of ethylbenzene by the catalytic dehydrogenation of cycloolefins which are present in a styrene stream.

A well-known problem in the production of styrene-butadiene rubber is a build up of vinylcyclohexene, hereinafter referred to as VHC, which causes the appreciable induction in the polymerization of butadiene and styrene, and tends to form a coagulant in the latex.

One problem with the conversion of a cycloolefin to an ethylbenzene, when the cycloolefin is in the presence of styrene, has been the polymerization of the styrene. The polymerization of styrene is a free-radical vinyl polymerization reaction, typically catalyzed by the presence of small amounts of an initiator.

Alkali metals are known initiators. The most simple initiators based on alkali metals are the free metals themselves. They are employed either in solutions or as dispersions. To create a large reaction surface, the alkali metal is coated on an inert carrier such as aluminum oxide.

Alkali metal catalyzed polymerization of styrene in hydrocarbon media and minor proportions of polar substances have been known. Such alkali metals are sodium, potassium and lithium.

VCH is formed by the thermal dimerization of unpolymerized butadiene. On a commercial scale, the amount of VCH in a styrene stream can reach 6% in the warmer months of the year.

There are many known processes for diolefin dimerization. One known process for the dimerization or codimerization of diolefin is in the liquid phase in an inert solution using a catalyst comprising a complex obtained by reacting the alkali metal or alkaline earth metal salt of a tricarbonyl nitrosyl ferrate anion with a metal halogen or pseudo halogen or complex thereof. This process operates at a temperature ranging from 20° to about 120° C.

Another known process teaches a liquid phase dimerization or co-dimerization of a diolefin which involves maintaining a diolefin in the solution of an inert solvent in contact with a catalyst which comprises a product of the interaction of two metal complexes, each of which is a nitrosyl and/or carbonyl ligand, wherein the interaction product contains at least one nitrosyl group. This process uses the catalyst in a liquid phase.

One known method for the production of ethylbenzene addresses those cycloolefins where the ring structure contains six carbon atoms and at least one double bond. The cycloolefins are treated at temperatures of about 20° to 150° C. and under pressures of about 0.8 to 2 atmospheres with an aromatization catalyst containing 5 to 25 percent by weight of an alkali metal and 75 to 95 percent by weight of aluminum oxide as the support. This method teaches that the specific surface area of the support material should generally be larger than 25 meters$^2$/gram, preferably larger than 100 meters$^2$/gram. This catalyst composition is directed to those alkali metals selected from the group consisting of lithium, sodium, potassium, rubidium, cesium, and mixtures of the aforementioned alkali metals.

SUMMARY OF THE INVENTION

Disclosed is a method for the production of ethylbenzene by catalytic dehydrogenation of cycloolefins having 8 carbon atoms and two double bonds wherein the cycloolefin is in the presence of a styrene stream comprising passing said stream at a temperature from about 160° C. to about 400° C. over an alkali metal complex catalyst.

The present invention is a process for the production of ethylbenzene from an 8 carbon atom cycloolefin wherein said cycloolefin is in the presence of a styrene stream.

More specifically, the present invention involves a process in which a hydrocarbon stream containing styrene and vinylcyclohexene is passed over an alkali metal complex catalyst whereby the VCH is selectively transformed into ethylbenzene without appreciable polymerization of the styrene.

DESCRIPTION OF PREFERRED EMBODIMENTS

The starting materials are eight carbon atom cycloolefins with two double bonds in the presence of a styrene stream. Examples of such cycloolefins include, but are not limited to: isomeric ethylidenecyclohexenes especially cis- and trans-(1)-ethylidene-cyclohexane-(2), the isomeric ethylcyclohexadienes especially 1-ethylcyclohexadiene-(1,3), 2-ethyl-cyclo-hexadiene-(1,3) and 1-ethyl-cyclohexadiene-(1,4), the isomeric vinylcyclohexenes, especially 1-vinylcyclohexene-3.

Representative of the alkali metal complex catalyst that are useful in the process of this invention are sodium carbonate, potassium carbonate, lithium carbonate, rubidium carbonate, potassium hydroxide, sodium hydroxide and lithium hydroxide or mixtures thereof. Preferably, sodium carbonate or potassium carbonate are used since they are less costly.

The alkali metal complex can be dispersed on a support. Supporting the alkali metal complex on a carrier is desired since this provides good surface area of catalyst per gram of material.

Representative of the carriers upon which the alkali metal complexes can be supported are aluminum oxide ($Al_2O_3$); silica; magnesium oxide (MgO); carbon (C) and titanium dioxide ($TiO_2$); however, any support that does not detrimentally effect the activity of the alkali metal complex and has a good surface area of at least 10 m$^2$/gm may be used.

Aluminum oxide ($Al_2O_3$) and magnesium oxide (MgO) are the preferred supports for the alkali metal complex. For the production of the support a great variety of modifications of aluminum oxide are suitable, such as α—, K—, H—, γ—, ϑ —, or β— modifications; however, aluminum oxide is generally preferred since it is easiest in its manipulation and yields satisfactory results.

To ensure good efficiency of the catalyst, the specific surface area of the support material should generally be larger than 10 m$^2$/g, preferably larger than 20m$^2$/g.

The catalyst may contain from about 2 to about 30 percent by weight of the alkali metal complex (based on a finished catalyst). Accordingly, the support comprises from 98 to 70 percent based on the finished catalyst. Preferably, the catalyst contains about 10 to about 20 percent by weight of the alkali metal complex.

The manufacturing method for catalysts containing alkali metals on an aluminum oxide support have been well-known to those skilled in the art for years. In a preferred embodiment, the catalyst is prepared by initially drying the support and loading the catalyst on the support by means of a simple dispersion using water as the dispersion medium. After the catalyst is loaded on the support, the catalyst and support is heated to remove the residual water.

After the manufacture of the catalyst, it is present in the form of a powder, particles extrudates or granules, depending on type of support.

The present invention can be conducted continuously, semi-continuous, or in a batch process. In this aspect, various modifications of the process can be used while remaining within the scope of the invention.

The reaction is ordinarily conducted in a protective gas atmosphere of nitrogen.

The reaction should be carried out with a pressure of at least 0.9 atmosphere and preferably at atmospheric pressure.

The LHSV of the volume of the feed stream is measured as the stream approaches the catalyst or preheater. Liquid hour space velocity, hereinafter known as LHSV, is meant to mean a volume of liquid throughout per gross volume of catalyst which is the actual volume plus the interstitial volume. For example, 90 ml of liquid feed stock is passed over 45 cc (gross volume) of catalyst in one hour to yield an LHSV valve of 2. See *Chem. Eng. Kinetics*, J. M. Smith, McGraw-Hill, N.Y., pp 99–100 (1956). As one skilled in the art would realize, if one has an excessive LHSV, the residence time of the feed stream with the catalyst will be insufficient to convert the VCH to ethylbenzene. Accordingly, if the LHSV value is too low, it results in a residence time which would be commercially unfeasible. Preferably the LHSV value is from about 0.30 to about 1.5.

In practice of the present invention, the styrene stream is in a gaseous phase, with the reaction temperature ranging from about 160° to about 450° C., preferably from about 300° to about 400° C. Excessive hydrocarbon cracking and styrene polymerization will occur in excess of 400° C. In view of Table I, various preferred reaction temperatures depend on the catalyst used in the present invention.

A particularly suitable type of operation comprises a fixed bed type in which the catalyst is disposed as a bed in a reaction zone provided with gas outlet means and the unsaturated hydrocarbon containing a six membered carbon atom ring passed therethrough in either an upward or downward flow. The unsaturated hydrocarbon stream may be heated while in the reaction zone or preferably may be heated prior to entering the zone containing the catalyst and kept at the desired temperature while therein.

The following examples are supplied in order to illustrate, but not necessarily to limit, the process of our invention. The data of the following table were obtained through the use of a stainless steel tubular reactor that was charged with 45 cc of catalyst and flushed with a constant flow of 7 milliliters/min of nitrogen gas. The styrene stream was charged in a down flow manner and vaporized over a glass bead pre-reactor zone prior to the catalyst bed. The hydrocarbon flow-rate was set with a Milton-Roy minipump and the pressure in the system was held at atmospheric. The reactor was equipped with thermocouples to monitor the inside and wall temperatures. The stream was passed over the catalyst after the reaction temperature had been obtained. The nitrogen flow was held constant at 7 milliliters per min. The entire effluent of the reactor was collected in a dry ice - acetone bath, which showed excellent mass balances. Heptane was used as a gas chromatographic internal standard in all cases.

The percent VCH conversion and percent ethylbenzene selectivity for all runs are present in the following table wherein conversion times selectivity equals yield.

While certain representative embodiments and details have been shown for the purpose of illustrating the invention, it will be apparent to those skilled in this art that various changes and modifications may be made therein without departing from the scope of the invention.

TABLE I

| Stream Styrene/VCH/Heptane | Reaction Temp (°C.) | VCH Conversion (%) | Ethylbenzene Selectively (%) | Styrene Recovered (%) | LHSV | Catalyst |
|---|---|---|---|---|---|---|
| EXAMPLE 1 | | | | | | |
| 72.6/15.7/11.7 | 200 | 5 | 0 | 100 | 0.30 | 25% Na$_2$CO$_3$/Al$_2$O$_3$ |
| " | 250 | 56 | 16 | 100 | " | " |
| " | 300 | 95 | 84 | 96 | " | " |
| " | 350 | 96 | 104 | 93 | " | " |
| " | 400 | 97 | 114 | 84 | " | " |
| " | 450 | 95 | 115 | 84 | " | " |
| EXAMPLE 2 | | | | | | |
| 78/14/8 | 300 | 79 | 95 | 100 | 1.5 | 10% Na$_2$CO$_3$/MgO |
| " | 325 | 88 | 100 | 100 | " | " |
| " | 350 | 100 | 110 | 89 | " | " |
| EXAMPLE 3 | | | | | | |
| 78/14/8 | 300 | 59 | 54 | 98 | " | 10% KOH/Al$_2$O$_3$ |
| " | 350 | 98 | 73 | 97 | " | " |
| " | 400 | 100 | 110 | 90 | " | " |
| EXAMPLE 4 | | | | | | |
| 62/22/15 | 300 | 90 | 86 | 100 | " | 10% K$_2$CO$_3$/Al$_2$O$_3$ |
| " | 350 | 100 | 93 | 100 | " | " |

We claim:

1. A method for the production of ethylbenzene by catalytic dehydrogeneration of cycloolefins having 8 carbon atoms and 2 double bonds which are present in a styrene stream comprising passing said stream at a temperature from about 160° to about 400° C. over an alkali metal complex catalyst.

2. A method for the production of ethylbenzene comprising catalytic dehydrogenating cycloolefins, having a 6 carbon atom ring with at least one double bond wherein said cycloolefin is in the presence of a styrene stream, by-passing said stream at a temperature from about 160° to about 400° C. over an alkali metal complex catalyst.

3. The method of claim 2 wherein said alkali metal complex catalyst is on a support.

4. The method of claim 3 wherein the alkali metal complex catalyst is from about 2 to about 30 percent by weight and support is 98 to about 70 percent by weight.

5. The method of claim 4 wherein the support is selected from the group comprising titanium dioxide, aluminum oxide, magnesium oxide, silica and carbon.

6. The method of claim 2 wherein the alkali metal complex catalyst is selected from the group consisting of lithium carbonate, potassium carbonate, sodium carbonate, rubidium carbonate, potassium hydroxide, sodium hydroxide, and lithium hydroxide.

7. The method of claim 3 wherein the alkali metal complex catalyst is sodium carbonate and the support is aluminum oxide.

8. The method of claim 3 in which the alkali metal complex catalyst is sodium carbonate and the support is magnesium oxide.

9. The method of claim 3 in which the alkali metal complex catalyst is potassium hydroxide and the support is aluminum oxide.

10. The method of claim 2 in which the alkali metal complex catalyst is potassium carbonate and the support is aluminum oxide.

11. A method for the production of ethylbenzene comprising passing a styrene stream containing vinylcyclohexene, at a temperature of from 160° C. to about 400° C. and under a pressure of at least 0.9 atmosphere, over an alkali metal complex catalyst.

12. A method of claim 2 wherein said styrene stream has a LHSV value of at least 0.2.

13. A method of claim 2 wherein said styrene stream has a LHSV value of from 0.3 to about 1.5.

14. A method for the production of ethylbenzene which comprises contacting a cycloolefin, having a 6 carbon ring with at least one double bond, wherein said cycloolefin is in the presence of styrene stream, with an alkali metal complex catalyst on a support that has a surface area of at least $10m^2$, at a temperature of from 300° to 400° C.

15. A process according to claim 14 wherein the cycloolefin is selected from the group consisting of cis-(1)-ethylidene-cyclohexene-(2), trans-(1)-ethylidene-cyclohexene-(2), 1-ethyl-cyclohexadiene-(1,3), 2-ethyl-cyclo-hexadiene-(1,3), 1-ethylcyclohexadiene-(1,4), and 1-vinylcyclohexene-3.

* * * * *